(12) United States Patent
Kuhn et al.

(10) Patent No.: US 8,445,225 B2
(45) Date of Patent: May 21, 2013

(54) METHODS FOR THE DETECTION OF CIRCULATING TUMOR CELLS

(75) Inventors: Peter Kuhn, Solana Beach, CA (US);
John Ho Griffin, Del Mar, CA (US);
Kelly Bethel, San Diego, CA (US);
Dena Marrinucci, Del Mar, CA (US)

(73) Assignee: The Scripps Research Institute, La Jolla, CA (US)

( * ) Notice: Subject to any disclaimer, the term of this patent is extended or adjusted under 35 U.S.C. 154(b) by 144 days.

(21) Appl. No.: 12/553,733

(22) Filed: Sep. 3, 2009

(65) Prior Publication Data

US 2010/0247492 A1 Sep. 30, 2010

Related U.S. Application Data

(60) Provisional application No. 61/094,819, filed on Sep. 5, 2008.

(51) Int. Cl.
*C12Q 1/02* (2006.01)
*C12Q 1/68* (2006.01)
*G01N 33/53* (2006.01)

(52) U.S. Cl.
USPC .............................. 435/29; 435/6.14; 435/7.2

(58) Field of Classification Search
USPC ............................................ 435/29, 6.14, 7.2
See application file for complete search history.

(56) References Cited

U.S. PATENT DOCUMENTS

| | | |
|---|---|---|
| 6,197,523 B1 | 3/2001 | Rimm et al. |
| 6,365,362 B1 | 4/2002 | Terstappen et al. |
| 2002/0009759 A1 | 1/2002 | Terstappen et al. |
| 2002/0013262 A1 | 1/2002 | Alonso et al. |
| 2003/0129676 A1 | 7/2003 | Terstappen et al. |
| 2004/0202665 A1* | 10/2004 | Lazarovits et al. ........ 424/178.1 |
| 2007/0026419 A1* | 2/2007 | Fuchs et al. ........................ 435/6 |
| 2008/0206288 A1 | 8/2008 | Ostrand-Rosenberg et al. |

FOREIGN PATENT DOCUMENTS

| | | |
|---|---|---|
| WO | WO 2004/056978 A1 | 7/2004 |
| WO | WO 2007/089911 A2 | 8/2007 |
| WO | WO 2007/089911 A3 | 8/2007 |

OTHER PUBLICATIONS

Quax et al (Protein and Messenger RNA levels of Plasminogen Activators and inhibitors Analyzed in 22 Human Tumor Cell Lines. 1990. Cancer Research 50: 1488-1494).*
Biggerstaff et al (Soluble fibrin augments platelet/tumor cell adherence in vitro and in vivo and enhances experimental metastatsis. Clinical and Experimental Metastasis 1999 17: 723-730).*
Atkin et al., "Hypotonic lysis of red blood cell contamination from human anterior pituitary adenoma cell preparations", *In Vitro Cell. Dev. Biol. Anim.*, 31(9):657-658 (1995).
Hsieh et al., "High speed detection of circulating tumor cells", *Biosens. Bioelectron.*, 21(10):1893-1899 (2006).
Krivacic et al., "A rare-cell detector for cancer", *Proc. Natl. Acad. Sci. USA.*, 101(29):10501-10504 (2004).
Marrinucci et al., "Case study of the morphologic variation of circulating tumor cells", *Hum. Pathol.*, 38(3):514-519 (2007).
Cristofanilli et al., "Circulating tumor cells, disease progression, and survival in metastatic breast cancer", *N. Engl. J Med.*, 351(8):781-791 (2004).
Rimler et al., "Nuclear exclusion of the androgen receptor by melatonin", *J. Steroid Biochem. Mol. Biol.*, 81(1):77-84 (2002).
Tu et al., "Biochemical characterization of atroxase and nucleotide sequence encoding the fibrinolytic enzyme", *Toxicon*, 34(11-12):1295-1300 (1996).
Varki A. & Varki N.M., "P-selectin, carcinoma metastasis and heparin: novel mechanistic connections with therapeutic implications", *Braz. J. Med. Biol. Res.*, 34(6):711-717 (2001).
Yamaguchi et al., "Significant detection of circulating cancer cells in the blood by reverse transcriptase-polymerase chain reaction during colorectal cancer resection", *Ann. Surg.*, 232(1):58-65 (2000).

* cited by examiner

*Primary Examiner* — Karen Cochrane Carlson
*Assistant Examiner* — Natalie Moss
(74) *Attorney, Agent, or Firm* — DLA Piper LLP (US)

(57) ABSTRACT

The present invention provides methods for revealing, detecting, and analyzing circulating tumor cells in the blood of a subject. Revealing detectable circulating tumor cells allows for early stage detection and diagnosis in addition to long term prognosis in subjects with cancer. Additionally, enrichment allows for robust detection and clinically meaningful analysis of low volume samples for use in clinical settings as well as innovative methods for the treatment of cancers.

33 Claims, 9 Drawing Sheets

A

B

C

A

B

C

METHODS FOR THE DETECTION OF CIRCULATING TUMOR CELLS

CROSS REFERENCE TO RELATED APPLICATION(S)

This application claims the benefit under 35 USC §119(e) of U.S. Application Ser. No. 61/094,819, filed Sep. 5, 2008, the entire content of which is incorporated herein by reference.

GRANT INFORMATION

This invention was made with government support under Grant No. CA125653 awarded by the National Institutes of Health/National Cancer Institute. The government has certain rights in the invention.

BACKGROUND OF THE INVENTION

1. Field of the Invention

The present invention relates generally to cancer diagnostics and more specifically to methods for revealing circulating tumor cells (CTCs) allowing for robust clinical analysis of low volume samples.

2. Background Information

Circulating tumor cells (CTCs) are generally, although not exclusively, epithelial cells that originate from a solid tumor in very low concentration into the blood stream of patients with various types of cancer. The shedding of CTCs by an existing tumor or metastasis often results in formation of secondary tumors (see FIG. 1). Secondary tumors typically go undetected and lead to 90% of all cancer deaths. Circulating tumor cells provide the link between the primary and metastatic tumors. This leads to the promise of using the identification and characterization of circulating tumor cells for the early detection and treatment management of metastatic epithelial malignancies. Detection of CTCs in cancer patients offers an effective tool in early diagnosis of primary or secondary cancer growth and determining the prognosis of cancer patients undergoing cancer treatment because number and characterization of CTCs present in the blood of such patients has been correlated with overall prognosis and response to therapy (see FIGS. 2 and 3). Accordingly, CTCs serve as an early indicator of tumor expansion or metastasis before the appearance of clinical symptoms.

While the detection of circulating tumor cells (CTCs) has important prognostic and potential therapeutic implications in the management and treatment of cancer, because of their occult nature in the bloodstream, these rare cells are not easily detected. CTCs were first described in the 1800s, however only recent technological advances have allowed their reliable detection. CTCs are thought to exist in peripheral blood at ultra-low concentrations of patients with tumors. For example, for patients with carcinomas it is estimated that every one in ten million normal blood cells is a CTC. While existing technology can identify CTCs and correlate them with disease, no method has sufficient sensitivity to reliably measure a statistically significant number of cells at varying stages of the disease to guide the most effective treatment regime.

The first automated system developed to enumerate CTCs, was put on the market in 2004 and uses immunomagnetic enrichment technology. More recent methodologies have challenged this system as the "gold standard" for enumeration of CTCs, finding a factor of 10-100 times more CTCs. The reason(s) behind this apparent discrepancy in the numbers of CTCs found per blood sample with different methodologies is not understood, but has raised questions and concerns within the community of researchers and clinicians in this established field.

The most used methods for enumeration/characterization of CTCs are immunomagnetic enrichment methods targeting the surface protein EpCam, fiber-optic array technology, and a recently developed "CTC chip".

With the use of immunomagnetic enrichment technology CTCs can be detected in between 45% and 50% of metastatic breast cancer patients. The most widely used methodology to detect CTCs utilizes immunomagnetic enrichment. The technology relies upon immunomagnetic enrichment of tumor cell populations using magnetic ferrofluids linked to an antibody which binds epithelial cell adhesion molecule (Ep-CAM), expressed only on epithelial derived cells. This methodology requires 7.5 mL of blood for analysis and finds greater than 2 CTCs in only some metastatic cancer patients as shown in the Table 1 below. Other studies have been done using negative enrichment, and other forms of positive enrichment, and have achieved similar results.

TABLE 1

Detection of CTCs in Various Types of Cancers Using Immunomagnetic Enrichment

| Types of Cancers | ≧2 CTCs found | Ave/7.5 mL | Ave/ml |
|---|---|---|---|
| Breast (n = 422) | 37% | 84 | 11 |
| Lung (n = 99) | 20% | 30 | 4 |
| Colorectal (n = 196) | 30% | 4 | 0.5 |
| Pancreatic (n = 16) | 19% | 2 | 0.3 |
| Prostate (n = 123) | 57% | 75 | 10 |
| HD (n = 345) | 1% | 0.1 | 0.01 |

Another method for enumeration/characterization of CTCs is Fiber-optic Array Scanning Technology (FAST). Using the FAST method, 7.5 mL of blood is needed for analysis. Red blood cells are lysed and nucleated cells are distributed as a monolayer on slides that can hold up to 30 million cells. There is no enrichment step in this methodology. Cells are fixed, permeabilized and stained with a pan anti-cytokeratin antibody-Alexa Fluor 555, CD45-Alexa Fluor 647, and DAPI (nuclear stain). FAST scans each slide and identifies the location of each red fluorescent object on the slide. Each fluorescent object is imaged via an automated digital microscope and CTCs are enumerated as being CK+, CD45−, DAPI+ cells. This methodology has been tested on a variety of metastatic cancer patients, including breast, lung, prostate, colorectal, and pancreatic. Similar CTC counts are found using this method as compared to methods using immunomagnetic enrichment.

Another method for enumeration/characterization of CTCs is microfluidic or "CTC-Chip" technology. The methods utilizes 1-3 mL of blood in which whole blood flows past 78,000 EpCam-coated microposts. EpCam+ cells stick to the posts and are subsequently stained with cytokeratin, CD45, and DAPI. With this methodology, CTCs are found in virtually all metastatic cancer patients at a relatively high purity and not in healthy controls. Additionally, CTC-chip technology identifies CTCs in all patients and in higher numbers than other technologies by a factor of approximately 10 to 100 fold as reported in two recent publications shown in Tables 2 and 3 below.

TABLE 2

Identification of CTCs Using CTC-Chip Technology

| Types of Cancers | Range/mL | Ave/mL | Ave Purity* |
|---|---|---|---|
| Breast (n = 10) | 5 to 176 | 79 | 60% |
| NSCLC (n = 55) | 5 to 1,281 | 155 | 52% |
| Prostate (n = 26) | 16 to 292 | 86 | 49% |
| Pancreatic (n = 15) | 9 to 831 | 196 | 53% |
| Colorectal (n = 10) | 42 to 375 | 121 | 67% |
| HD (n = 20) | 0 | n/a | n/a |

*Purity is the ratio between cells attached to the EpCam posts that are CK+ versus CD45+

TABLE 3

Identification of CTCs Using CTC-Chip Technology

| Type of Cancer | Range/mL | Ave/mL | Ave Purity |
|---|---|---|---|
| Non-small cell lung carcinoma NSCLC (n = 23) | 5 to 771 | 74 | not reported |

Although all of the CTC detection approaches are currently in use, significant limitations have been identified with the current approaches. One limitation is that the number of CTCs detected per sample using current methods is too low to provide robust interpretation or clinically meaningful content of a particular sample. Additional limitations of current methods include low CTC detection due to CTC heterogeneity. For example, differences in individual CTC features within the CTC population of interest further hinder the number of CTCs detected using current methodologies. Such differences may include size variations between individual CTCs, and variable or down regulated expression between individual CTCs of the cell surface markers used to detect CTCs.

SUMMARY OF THE INVENTION

The present invention is based in part on the seminal discovery of innovative methods for the processing and preparation of blood that reveals detectable circulating tumor cells. Accordingly, the present invention provides methods for improved detection allowing for the robust detection and clinically meaningful analysis of samples for use in clinical, research and development settings as well as innovative methods for the treatment of cancers.

Accordingly, in one embodiment, the invention provides a method for revealing circulating tumor cells in a sample. The method includes removing, degrading or altering a protein, carbohydrate, cell, or a combination thereof, aggregated, or in physical association with, the surface of the circulating tumor cells to unmask the cell, thereby revealing the circulating tumor cell. In one aspect, revealing the cells includes removing, degrading or altering blood plasma proteins, carbohydrates, platelets, other blood cells, or a combination thereof. In an exemplary aspect, the blood plasma factor is a clotting factor, such as fibrin. In various aspects, the cells may be unmasked and thereby revealed by treating the cells enzymatically (e.g., biochemical reaction mediated by an enzyme), mechanically (e.g., mechanical force), electrically (e.g., electrical force), electromagnetically (e.g., electromagnetic radiation of the electromagnetic spectrum), chemically, or any combination thereof. In an exemplary aspect the cells are treated enzymatically by fibrinolysis with plasmin. In various other aspects, the revealed cells may be further analyzed by image analysis and/or detection of cell surface markers.

In another embodiment, the invention provides a method for diagnosing or prognosing cancer in a subject. The method includes revealing circulating tumor cells of the subject by removing, degrading or altering proteins, carbohydrates, cells, or a combination thereof, aggregated, or in physical association with, the surface of the circulating tumor cell to unmask the cells thereby revealing the circulating tumor cells. The revealed circulating tumor cells may then be analyzed to diagnose or prognose cancer in a subject.

In another embodiment, the invention provides a method for treating cancer. The method includes revealing circulating tumor cells in a subject including removing, degrading or altering proteins, carbohydrates, cells, or a combination thereof, aggregated, or in physical association with, the surface of the circulating tumor cell in the subject. The revealed CTC may then be administered to the subject alone or in combination with another therapeutic agent.

In another embodiment, the invention provides a method for treating cancer in vivo. In this embodiment, the patient is treated with an unmasking agent, which makes the circulating tumor cells within the patient more accessible to chemotherapy or immune system response. The unmasking agent may be a chemical, an antibody or an enzyme which directly or indirectly effectuates removal or alteration of bound protein, carbohydrates or other cells; including platelets, associated with the surface of the CTC, or which directly or indirectly blocks bound protein or other cells, including platelets, from binding to the surface of the CTC, making the CTC sensitive to the chemotherapy or immune system response.

In another embodiment, the invention provides a composition including a revealed population of circulating tumor cell. In one aspect, the composition includes unlysed and/or intact cells. In another aspect, the revealed population includes greater than about 5, 7.5, 10, 50, 100, or 200 circulating tumor cells per 100 microliters of sample.

In another embodiment, the invention provides a method for determining responsiveness of a subject to a therapeutic regime. The method includes revealing circulating tumor cells of the subject including removing, degrading or altering proteins, carbohydrates, cells, or a combination thereof, aggregated, or in physical association with, the surface of the circulating tumor cell to unmask the cells, thereby revealing the circulating tumor cells for detection, capture, enrichment, analysis, and the like. The revealed cells may then be analyzed to determine the responsiveness of the subject to a therapeutic regime. In one aspect, the analysis may include detecting one or more cell surface markers. In another aspect, analysis may include image analysis. In one aspect, the analysis includes detection of markers such as EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, or Leukocyte Associated Receptor (LAR).

In another embodiment, the invention provides a method for characterizing CTCs and, by inference, the tumor or tumors from which they are derived. In this embodiment, CTCs are revealed thus making a cell-specific marker available for detection and/or accurate quantification. This method includes treating the cells enzymatically (e.g., biochemical reaction mediated by an enzyme), mechanically (e.g., mechanical force), electrically (e.g., electrical force), electromagnetically (e.g., electromagnetic radiation of the electromagnetic spectrum), chemically, or any combination thereof to remove or alter platelets, proteins, carbohydrates, cells or other biomolecules associated with the surface of the circulating tumor cells to reveal surface proteins, or other cell-specific markers, on the cell for characterization via specific interaction with a marker molecule. In one embodiment, the marker molecule is an antibody against a specific protein or epitope thereof. In another embodiment the marker molecule is an aptamer against a specific protein or epitope thereof. In another embodiment the marker molecule is an oligonucleotide probe capable of hybridizing with a specific nucleotide sequence. In another embodiment the marker molecule is a molecule against a specific cell type. Accordingly, characterization of a CTC may be performed via analysis of a cellular component outside the cell membrane, and also include analysis of intracellular components.

In various aspects of the invention, the characterization of a circulating tumor cell includes determining the presence or absence of a surface protein, quantifying the amount of a surface protein, and/or detecting a change in a surface protein. A change in a surface protein could be for instance a mutation or a difference in post-translation modification. In one aspect, the analysis includes detection or characterization of cell-surface markers such as EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, or Leukocyte Associated Receptor (LAR). In another aspect, the characterization of a CTC determines the responsiveness to a therapeutic regime.

In another embodiment, the invention provides a method to better detect CTCs using standard enrichment and enrichment free techniques, such as those involving immunospecific interactions, immunomagnetic capture, solid support capture, filtration, and the like. The method includes revealing circulating tumor cells in a sample and subsequently performing a conventional enrichment, thereby increasing the amount of CTCs after the enrichment by 25%, 50%, 100%, 200%, 500% or more as compared to an enriched sample in which the CTCs were not initially revealed. Alternatively, CTCs enriched using a conventional technique may be subjected to the methods described herein to reveal (e.g., unmask) the CTCs, thereby increasing the amount of detectable CTCs by 25%, 50%, 100%, 200%, 500% or more as compared to an enriched sample in which the CTCs are not revealed as described herein.

In another embodiment, the invention provides a method for determining a candidate subject for a clinical trial. The method includes revealing of circulating tumor cells of the subject by removing, degrading or altering proteins, carbohydrates, cells, or a combination thereof, aggregated, or in physical association with, the surface of the circulating tumor cells to unmask the cells, thereby revealing of the circulating tumor cells. The revealed cells may then be analyzed to determine the candidate subject for a clinical trial. In one aspect, the analysis may include detecting one or more cell surface markers. In another aspect, analysis may include image analysis. In one aspect, the analysis includes detection of markers such as EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, or Leukocyte Associated Receptor (LAR).

In another embodiment, the invention provides a method for determining the effectiveness of a candidate agent in the treatment of cancer. The method includes revealing of circulating tumor cells of a subject being administered the candidate agent including removing, degrading or altering proteins, carbohydrates, cells, or a combination thereof, aggregated, or in physical association with, the surface of the circulating tumor cells to unmask the cells, thereby revealing the circulating tumor cells. The revealed cells may then be analyzed to determine the effectiveness of the candidate agent in the treatment of cancer. In one aspect, the analysis may include detecting one or more cell surface markers. In another aspect, analysis may include image analysis. In one aspect, the analysis includes detection of markers such as EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, or Leukocyte Associated Receptor (LAR).

DETAILED DESCRIPTION OF THE INVENTION

The present invention relates generally to cancer diagnostics and therapy and more specifically to methods for revealing circulating cancer cells to make them more readily detectable and amenable to meaningful characterization thereby allowing for clinical analysis of samples as well as methods for the treatment of cancer.

The present invention is based, in part, on the expectation that a much larger number of CTCs are expected to be migrating in the blood of patients with metastasizing tumors than the numbers reported using current technologies. For example, migrating cells (CTCs) shed from a solid tumor are expected to be approximately 0.1% of the total number of tumor cells. A tumor of approximately 1 cubic centimeter in volume contains approximately 1 billion cells. Therefore, 1 million cells are expected to be migrating in a tumor that is metastasizing. As such, 2,000 CTCs are expected to be present per 10 mL of blood. However, existing technologies are capable of detecting only a fraction of this number limiting the ability to perform reliable clinical analysis and characterization of CTCs.

Figure 1:
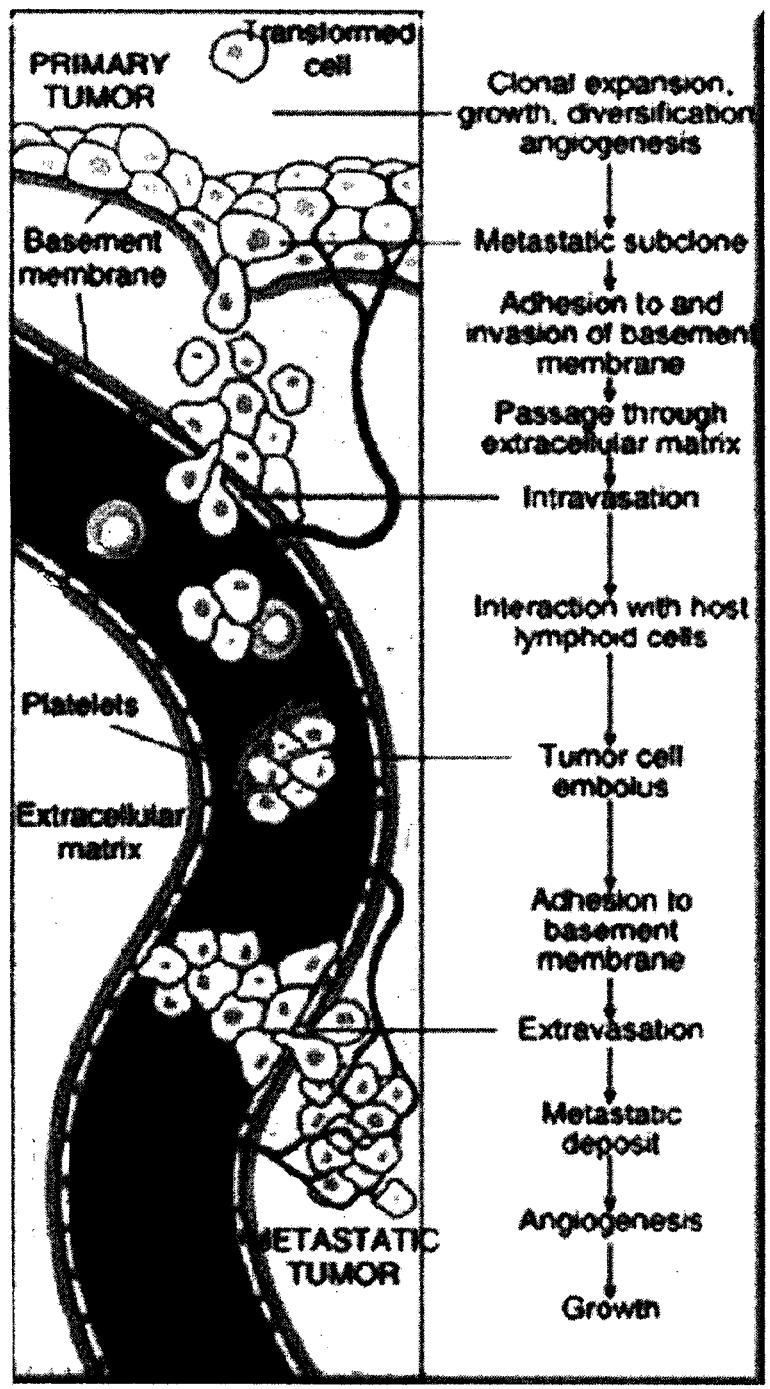
FIG. 1 is a pictorial representation of metastasis or the spread of cancer cells to distant areas of the body by way of the lymph system or bloodstream via circulating tumor cells.
Figure 2:
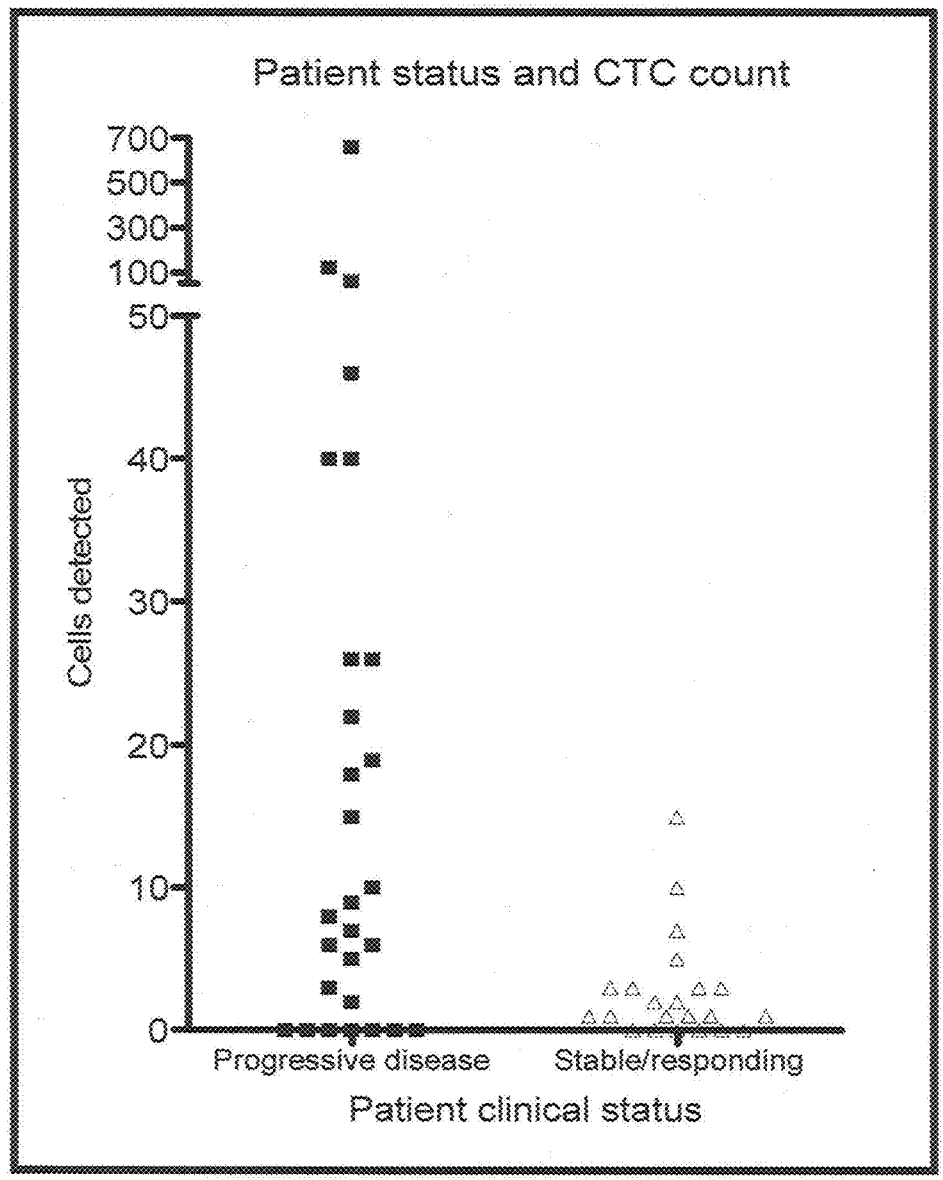
FIG. 2 is a graphical representation showing the correlation of CTC number with response to clinical treatment.
Figure 3:
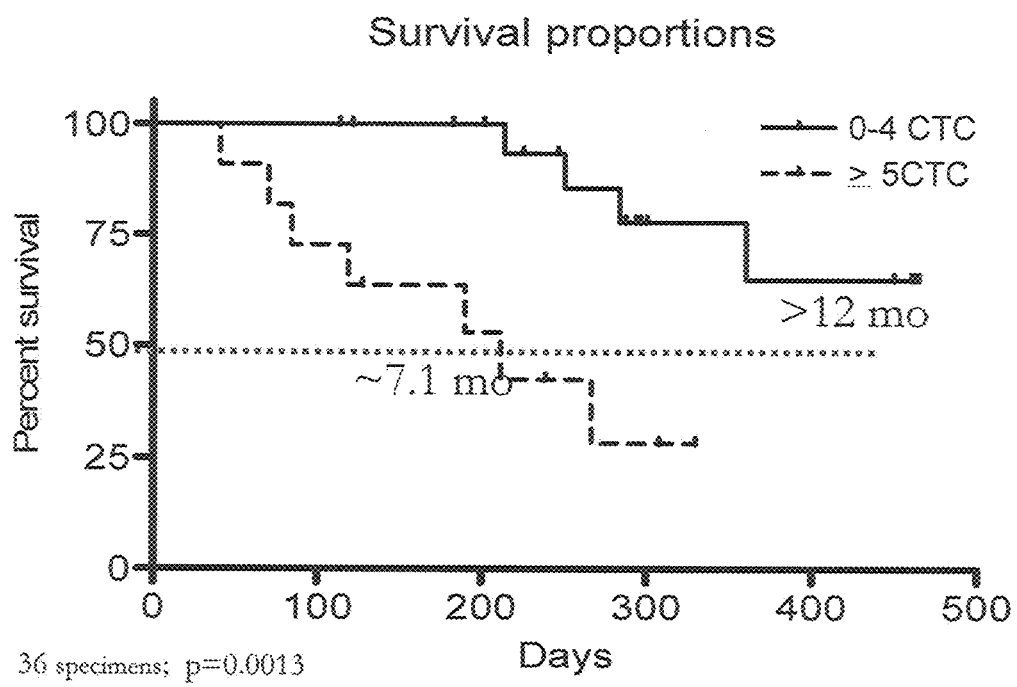
FIG. 3 is a graphical representation showing the correlation of CTC number with response to clinical treatment in patients with breast cancer.
Figure 4:
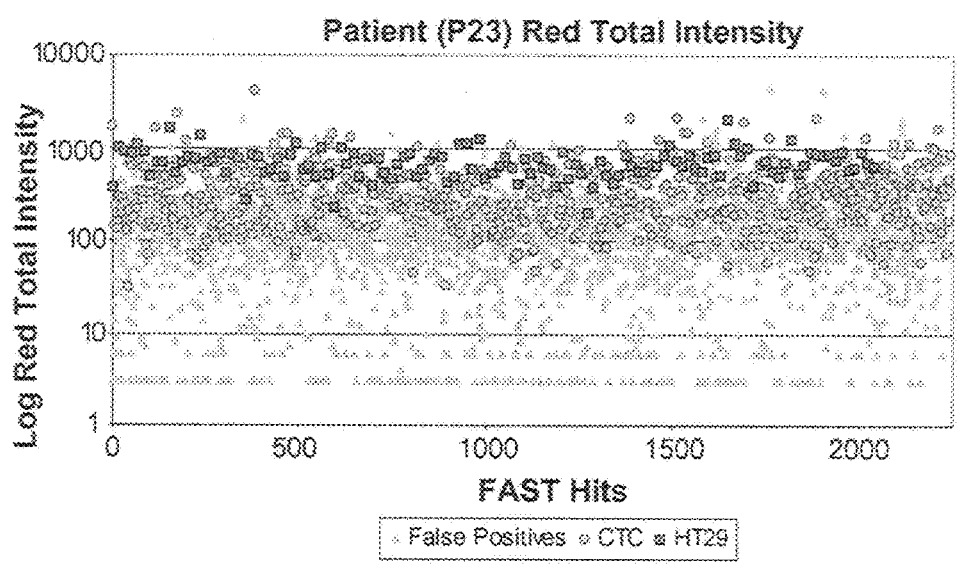
FIG. 4 is a graphical representation showing variable expression of cytokeratins between individual CTCs within a population of CTCs as compared with individual cells within a population of a human colon adenocarcinoma cell line (HT29).
Figure 5:
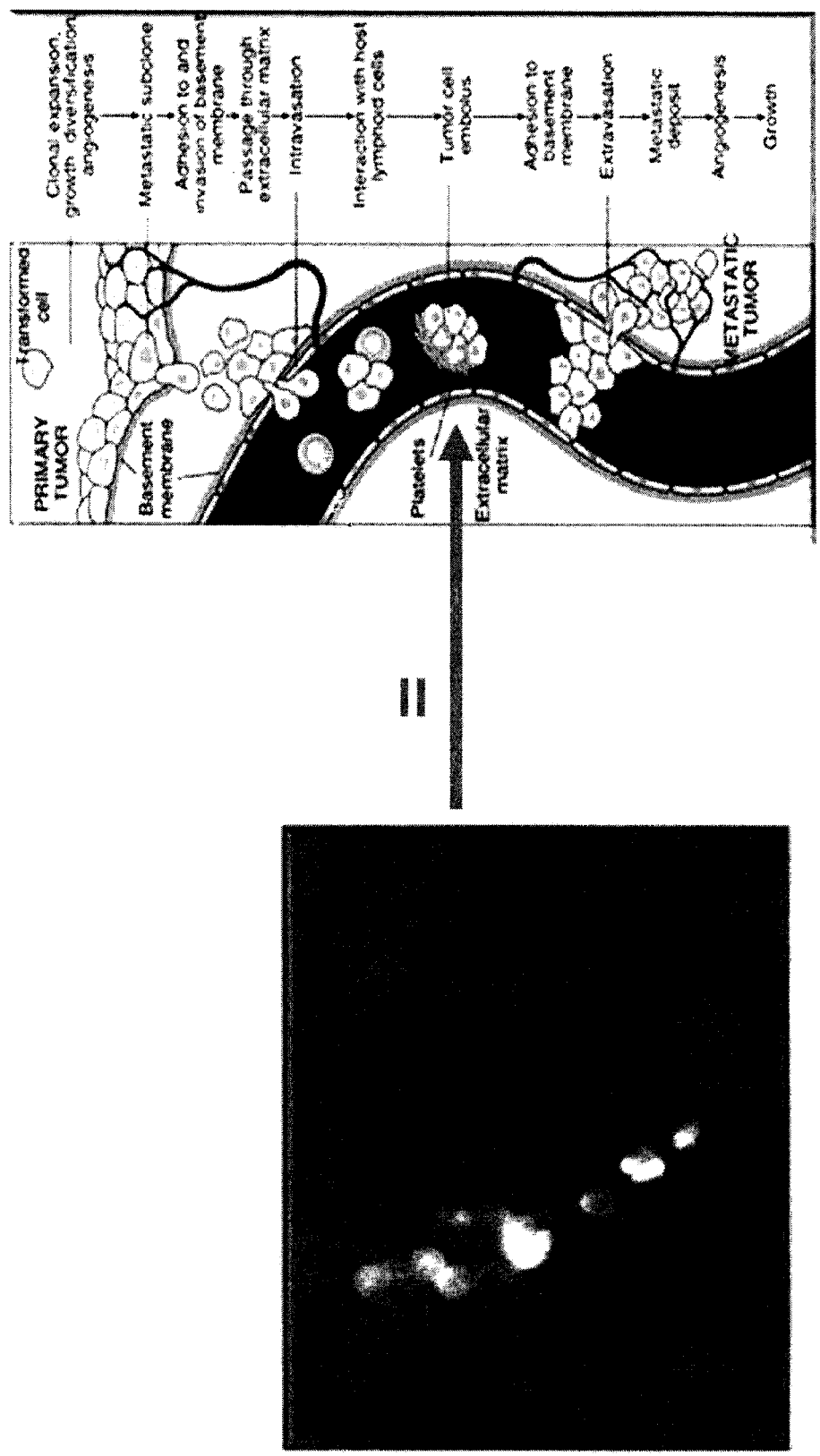
FIG. 5 is a pictorial representation of an image of a "cloaked" CTC aggregated with platelets.
Figure 6:
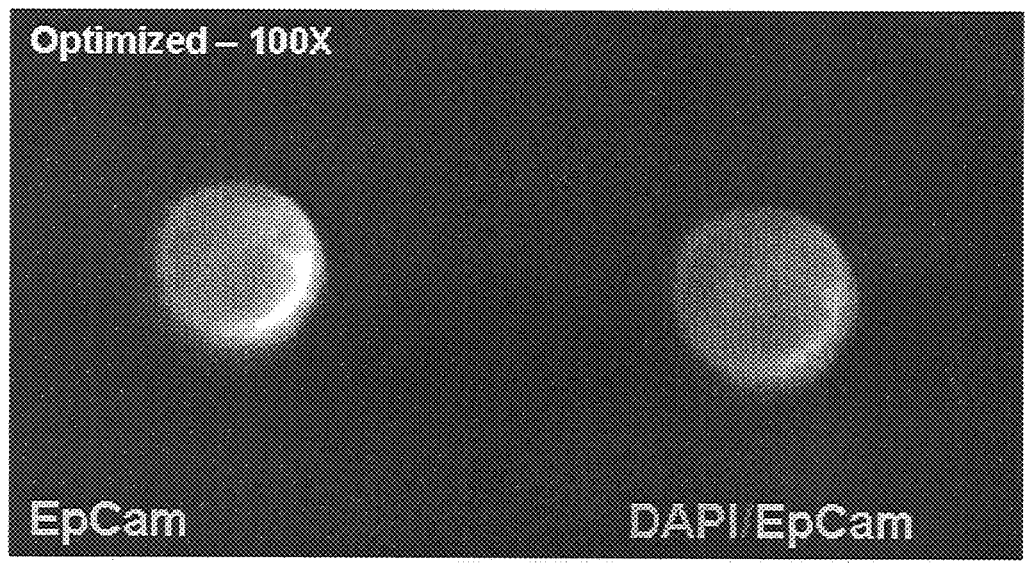
FIG. 6 is a pictorial representation of an optimized image of an unmasked CTC unaggregated with other cells or fibrous clots.

It was discovered that significant numbers of CTCs in circulation remain undetectable because they are "masked" or "cloaked" by cells, proteins, biomolecules and other factors aggregated at the surface of the CTCs shielding them from surface interactions and/or intracellular antibody binding as an effective immune escape mechanism. For example, platelets, fibrin, and other clotting proteins act as a "cloak device" to mask or veil critical cell surface markers on the surface of the cells allowing them to escape detection or observation using current methods which explain why such few CTCs are detected using current methods. Similarly, other factors can effectuate masking or veiling of CTCs such as, for example, glycosylation of surface protein markers or association of cell surface components with other biomolecules, such as lipids. For example, FIG. 5 shows an image of a cloaked CTC aggregated with platelets masking the surface of the CTC from detection. Alternatively, FIG. 6 shows an image of an unmasked CTC unassociated with other cells or fibrous clots which was revealed and processed using the methods described herein.

Accordingly, the present invention provides innovative methods for revealing CTCs, by, for example, "unmasking" CTCs allowing the CTCs to be detected or observed thus providing for reliable detection and identification of circulating tumor cells and subsequent characterization of these tumor cells for robust clinical analysis.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

In general, reference to "a circulating tumor cell" is intended to refer to a single cell, while reference to "circulating tumor cells" is intended to refer to more than one cell. However, one of skill in the art would understand that reference to "circulating tumor cells" is intended to include a population of circulating tumor cells including one or more circulating tumor cells.

The methods of the present invention generate revealed CTCs capable of detection. As used herein, the terms "revealing" and "revealing for" generally pertain to altering a CTC in its natural state so as to make the CTC more amendable to detection, analysis, characterization, and/or further processing, such as enriching. Revealing a CTC may include removing and/or degrading, all or some biomolecules aggregated and/or associated with the surface and/or surface components of the CTC. For example, revealing a CTC may include unmasking or unveiling the CTC by removing, degrading, or altering aggregated cells (e.g., platelets), carbohydrates, and/or proteins (e.g., fibrin) aggregated and/or physically associated with the surface of the CTC allowing access to one or more CTC cellular components, such as surface components, including for example, cancer surface markers and other surface bound cellular components, as well as intracellular components, such as nucleic acids and other intracellular components (e.g., nuclear and cytosolic proteins, and the like). As such, "unmasking" and/or "unveiling" are intended to include altering a feature of a CTC in its natural state that may assist in cloaking the CTC from immune recognition or response by the host and/or making the CTC more amendable to detection, analysis, characterization, and/or further processing. Revealing a CTC may include altering a CTC cellular component, such as an epitope of a cell surface marker, or protein physically associated and/or aggregated with the CTC.

The term "biomolecule" is intended to generally refer to any organic or biochemical molecule that occurs in a biological system.

CTCs may be revealed in any suitable sample type. As used herein, the term "sample" refers to any sample suitable for the methods provided by the present invention. The sample may be any sample that includes CTCs suitable for detection. Sources of samples include whole blood, bone marrow, pleural fluid, peritoneal fluid, central spinal fluid, urine, saliva and bronchial washes. In one aspect, the sample is a blood sample, including, for example, whole blood or any fraction or component thereof. A blood sample, suitable for use with the present invention may be extracted from any source known that includes blood cells or components thereof, such as venous, arterial, peripheral, tissue, cord, and the like. For example, a sample may be obtained and processed using well known and routine clinical methods (e.g., procedures for drawing and processing whole blood). In one aspect, an exemplary sample may be peripheral blood drawn from a subject with cancer.

The term "blood component" is intended to include any component of whole blood, including red blood cells, white blood cells, platelets, endothelial cells, mesothelial cells or epithelial cells. Blood components also include the components of plasma, such as proteins, lipids, nucleic acids, and carbohydrates, and any other cells that may be present in blood, due to pregnancy, organ transplant, infection, injury, or disease.

The term "cancer" as used herein, includes a variety of cancer types which are well known in the art, including but not limited to, dysplasias, hyperplasias, solid tumors and hematopoietic cancers. Many types of cancers are known to metastasize and shed circulating tumor cells or be metastatic, for example, a secondary cancer resulting from a primary cancer that has metastasized. Additional cancers may include, but are not limited to, the following organs or systems: brain, cardiac, lung, gastrointestinal, genitourinary tract, liver, bone, nervous system, gynecological, hematologic, skin, breast, and adrenal glands. Additional types of cancer cells include gliomas (Schwannoma, glioblastoma, astrocytoma), neuroblastoma, pheochromocytoma, paraganlioma, meningioma, adrenalcortical carcinoma, medulloblastoma, rhabdomyoscarcoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia; and skin cancers including malignant melanoma, basal cell carcinoma, squamous cell carcinoma, Karposi's sarcoma, moles dysplastic nevi, lipoma, angioma, dermatofibroma, keloids, sarcomas such as fibrosarcoma or hemangiosarcoma, and melanoma.

The term "circulating tumor cell" (CTC) is intended to mean any cancer cell that is found in a subject's sample. Typically CTCs have been exfoliated from a solid tumor. As such, CTCs are often epithelial cells shed from solid tumors found in very low concentrations in the circulation of patients with advanced cancers. CTCs may also be mesothelial from sarcomas or melanocytes from melanomas.

As used herein, a cellular component is intended to include any component of a cell that may be at least partially isolated upon lysis of the cell. Cellular components may be organelles, such as nuclei, perinuclear compartments, nuclear membranes, mitochondria, chloroplasts, or cell membranes; polymers or molecular complexes, such as lipids, polysaccharides, proteins (membrane, trans-membrane, or cytosolic); nucleic acids, viral particles, or ribosomes; or other molecules, such as hormones, ions, cofactors, or drugs.

Revealed CTCs of the present invention are unmasked and/or altered from their natural state allowing detection and subsequent characterization of the CTCs. As discussed herein, the CTCs may be unmasked and revealed by removing, degrading, and/or altering aggregated cells (e.g., platelets), carbohydrates, and/or proteins (e.g., fibrin) allowing access to critical components of the CTC critical to detection and/or analysis, such as, but not limited to surface components such as cancer markers and other surface bound cellular components.

Accordingly, a sample including revealed CTCs or a revealed CTC population is intended to mean a sample in which the sample has been processed as described herein to increase the relative population of revealed (e.g., unmasked and/or altered) CTCs as compared to if the sample had not been processed, for example, relative to an unprocessed sample. For example, the relative population of revealed CTCs in a sample may be increased by at least about 10%, 25%, 50%, 75%, 100% or by a factor of at least 2, 5, 10, 20, 30, 40, 50, 60, 70, 80, 90, 100, or even 200. In an exemplary aspect, a sample is produced including a revealed population of CTCs increased by a factor of about 10 or 100. In another exemplary aspect, a sample is produced including a revealed population of CTCs that remain intact and/or unlysed and are increased by at least about 10%, 25%, 50%, 75%, 100% or by a factor of at least 2, 5, 10, 20, 30, 40, 50, 60, 70, 80, 90, 100, or even 200.

Accordingly, in one embodiment, the invention provides a method for revealing of circulating tumor cells in a sample. The method includes removing, degrading, or altering proteins, carbohydrates, cells, or a combination thereof, in physical association with the surface of the circulating tumor cell to unmask the cells, thereby revealing of the circulating tumor cells in the sample.

Platelets cells, also known as thrombocytes, circulate in the blood and play an integral role with blood plasma proteins, such as clotting factors, in hemostasis leading to the formation of blood clots. Several clotting factors are known to be involved in clot formation and include, but are not limited to factors such as Factor V, Va, VII, VIIa, VIII, VIIIA, IX, IXa, X, Xa, XI, XIa, XI, XII, XIIa, XIII, XIIIa, prothrombin (II), thrombin, fibrinogen (I), and fibrin monomers and polymers.

It has been established that platelets, clotting factors such as fibrin, as well as other clotting proteins and cells, aggregate with CTCs and mask the CTCs surface thus masking detection and/or analysis. As discussed herein, a revealed CTC is intended to mean a CTC in which the aggregated platelets and clotting factors have been substantially removed or degraded thereby unmasking the CTC. In an exemplary aspect this is done without lysing the CTC to produce a revealed population of intact unmasked CTCs.

CTCs may be revealed and unmasked using a variety of known methods. For example, CTCs may be revealed using methods including treatments such as, but not limited to, enzymatic, mechanical, electrical, electromagnetic radiation, or chemical treatment, or any combination thereof.

In a preferred aspect, degradation of the proteins and/or cells from the surface of a CTC is performed by treating the CTCs enzymatically. Enzymatic treatment may occur by fibrinolysis. As used herein, fibrinolysis is intended to mean the enzymatic process wherein fibrin and/or products of coagulation, such as fibrin clots and the like are degraded. In one aspect, degradation by fibrinolysis is performed by treatment of CTCs with the enzyme plasmin. Plasmin is a serine protease present in the blood that degrades fibrin as well as other blood plasma proteins performing a crucial role in fibrinolysis. Plasmin is known to enzymatically cleave such proteins as fibrin, fibronectin, thrombospondin, laminin, and von Willebrand factor. A variety of natural and synthetic plasmins are well known in the art and may be used with the methods of the present invention so long as the enzyme retains some role in fibrinolysis.

Plasmin is derived from plasminogen which is excreted from the liver into the circulation. Once in the circulation, plasminogen may be activated by a variety of factors to generate plasmin, such as tissue plasminogen activator (tPA), urokinase plasminogen activator (uPA), thrombin, fibrin, and factor XII (Hageman factor). Accordingly, in another aspect of the invention, fibrinolysis is produced by enzymatic activation of plasminogen.

Fibrinolysis may also be effectuated by other naturally or synthetically occurring agents. For example, in yet another aspect of the invention fibrinolysis may occur by treatment of CTCs with a natural or synthetic animal venom or toxin. For example, venomous animals, such as but not limited to bats, snakes and insects are known to possess venom or toxins capable of direct or indirect enzymatic activation of fibrinolysis.

In addition to enzymatic degradation cells and proteins aggregated to the surface of masked CTCs, CTCs may be treated mechanically, electrically, or chemically. For example, mechanical forces may be used in the treatment of CTCs to shear cells and proteins aggregated to the surface. Accordingly, the present invention envisions treating CTCs with any type of mechanical force or movement capable of unmasking CTCs. Additionally, treatment with a variety of electrical forces may be utilized to unmask CTCs such as, but not limited to, electromagnetic, electrostatic, electrochemical, electroradiation, ultrasonic forces, and the like. Electromagnetic radiation may include application of radiation from any region of the electromagnetic spectrum.

In one embodiment, mechanical forces sufficient to reveal CTCs by breaking up agglomerated cells in physical association with the surface of CTCs may be generated in microfluidic devices used for biomedical and diagnostic research. The microscale devices that constitute a microfluidic system typically consist of a plurality of posts, grooves or microchannels, and chambers etched or molded in a substrate commonly composed of silicon, plastic, quartz, glass, or plastic. The size, shape, configuration of these microscale features, as well as their interconnections determine the physical forces generated on the constituents of a fluid sample flowing through the device, such as cells or clusters of cells suspended in the fluid. It is envisioned that the microscale features of a microfluidic device, along with factors, such as rate of fluid flow, may be configured and exploited to generate sufficient mechanical forces to reveal CTCs in a fluid sample. Additionally, one of skill in the art would recognize that CTCs may be treated with one or more other treatment techniques (e.g., enzymatically, chemically, electrically, and like), separate from, or in addition to the mechanical forces in the microfluidic system. Accordingly, CTCs may be treated enzymatically, chemically, or the like, before or after being introduced into a microfluidic device, as well as in the microfluidic device itself.

Further, treatment with a variety of chemical agents may be utilized to unmask CTCs. For example, chemical agents such as, but not limited to, natural or synthetic molecules, organic compounds, non-organic compounds, drugs, therapeutics, and the like may be used to activate or inhibit various steps in the fibrinolysis pathway leading to degradation of clotting factors. Additional chemical agents that may be used to unmask CTCs include anti-platelets, anti-coagulants and/or blood thinners which degrade and/or suppress the platelet and fibrin activation on the surface of CTCs. Common anti-platelets, anti-coagulants and blood thinners that may be used include but are not limited to, cyclooxygenase inhibitors, such as aspirin; adenosine diphosphate (ADP) receptor inhibitors, such as clopidogrel, and ticlopidine; phosphodiesterase inhibitors, such as cilostazol; glycoprotein IIB/IIIA inhibitors, such as abciximab, eptifibatide, tirofiban, and defibrotide; adenosine reuptake inhibitors such as dipyridamole; vitamin K antagonists; heparin and heparin derivative substances; clopidogrel (Plavix™); benzopyrone (coumarin); and direct thrombin inhibitors. In a preferred aspect, the CTCs are treated with heparin to reveal for the cells.

In various aspects, it may be necessary to limit the duration of treatment to prevent excess degradation that may impair the integrity of the CTCs leading to lysis. Accordingly, in various embodiments, cells should be treated for a time sufficient for removing molecules from the CTCs so that the cell can be further detected and/or identified. While this time may vary depending of the type of treatment applied to the cell, it is within the knowledge of one skilled in the art to determine such time by routine assay. Additionally, where CTCs are treated enzymatically or chemically, reactions may be controlled by addition of specific inhibitors to slow or stop reactions.

The total number of revealed CTCs included in a revealed CTC population is dependent, in part, on the initial sample volume. In various aspects, revealing of CTCs in a wide range of initial sample volumes is sufficient to produce a revealed number of CTCs capable of providing clinically significant results. As such, the initial sample volume may be less than about 25 µl, 50 µl, 75 µl, 100 µl, 125 µl, 150 µl, 175 µl, 200 µl, 225 µl, 250 µl, 300 µl, 400 µl, 500 µl, 750 µl, 1 ml, 2 ml, 3 ml, 4 ml, 5 ml, 6 ml, 7 ml, 8 ml, 9 ml or greater than about 10 ml. In an exemplary aspect, the initial sample volume is between about 100 and 200 µl. In another exemplary aspect, a sample processed as described herein includes greater than about 1, 2, 5, 7, 10, 15, 20, 30, 40, 50, 100, 200, 300, 400, 500, 600, 700, 800, 900, or even 1000 revealed CTCs.

Accordingly, in one embodiment, the invention provides a composition including a revealed (e.g., unmasked) population of circulating tumor cell. In one aspect, the composition includes unlysed and/or intact cells. In another aspect, the revealed population includes greater than about 5, 7.5, 10, 50, 100, or 200 circulating tumor cells per 100 microliters of sample.

In various embodiments of the present invention, revealed CTCs are analyzed to derive clinically significant data. Analysis of CTCs may be performed by a variety of methods depending of the type of data desired. For example, in various aspects, subsequent to revealing, CTCs may be analyzed by detecting and characterizing the CTCs via assays utilizing recognition and/or binding of cellular components, such as cell surface markers. A variety of detection/immobilization assays are contemplated for use with the present invention from which useful data may be derived. Additional analysis methods may include image analysis.

As used herein, image analysis includes any method which allows direct or indirect visualization of revealed CTCs and may be in vivo or ex vivo. For example, image analysis may include, but not limited to, ex vivo microscopic or cytometric detection and visualization of cells bound to a solid substrate, flow cytometry, fluorescent imaging, and the like. In an exemplary aspect, revealed CTCs are detected using antibodies directed to cell surface markers and subsequently bound to a solid substrate and visualized using microscopic or cytometric detection. Alternatively, revealed CTCs may be analyzed via imaging analysis in vivo by revealing CTCs in vivo by administering to a subject an agent described herein capable of activating fibrinolysis to unmask and reveal CTCs. Additionally, the CTCs may be revealed ex vivo and reinfused into the subject and subsequently analyzed via imaging analysis.

It is expected that unmasking to expose all or part of the cell surface of CTCs imparts a "stickiness" to the cells due to the unmasked cell surface area. Thus one of skill in the art would recognize that revealing CTCs to expose the cell surface imparts a characteristic that may be advantageous in various down-stream processes, such as analysis, detection, and enrichment. For example, the imparted "stickiness" may assist revealed CTCs in adhering to solid surfaces, such as slides or solid supports for immunofluorescent detection and analysis.

In one embodiment, the revealed cells adhere to a solid surface, such as a microscope slide. In some examples, the microscope slide has a surface covering such as polylysine or specially coated slides that promote cell attachment. The unmasking process removes the coating on the CTCs and breaks up aggregates of CTCs, allowing the CTCs to adhere to the solid surface.

In various embodiments, a variety of cell surface markers may be used to analyze and detect revealed CTCs. As used herein, cell surface markers include any cellular component that may be detected within or on the surface of a cell, or a macromolecule bound or aggregated to the surface of the cell. As such, cell surface markers are not limited to markers physically on the surface of a cell. For example, cell surface markers may include, but are not limited to surface antigens, transmembrane receptors or coreceptors, macromolecules bound to the surface, such as bound or aggregated proteins or carbohydrates, internal cellular components, and the like. In one aspect, the cell surface markers may be a cell adhesion molecule, such as EpCAM or a cytokeratin. In an exemplary aspect, the antibodies used to detect cell surface markers are anti-cytokeratin, pan-kerartin and anti-EpCAM.

Additionally, a number of cell surface markers known to be specific to cancers may be targeted or otherwise utilized to detect and analyze CTCs. For example, various receptors have been found to be expressed or over expressed only in particular type of cancers. In various aspects of the invention cell surface markers include EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, or Leukocyte Associated Receptor (LAR). Further, cell surface markers may be utilized that are specific to particular cell types. For example, useful endothelial cell surface markers include CD105, CD106, CD144, and CD146, while useful tumor endothelial cell surface markers include TEM1, TEM5, and TEM8.

In another embodiment, the revealed CTCs are captured by techniques commonly used to enrich a sample for CTCs, for example those involving immunospecific interactions, such as immunomagnetic capture. The process of revealing the CTCs makes the revealed CTCs more amenable to immunocapture by unmasking and/or exposing the surface markers used for immunocapture. A variety of immunocapture methods are known, including immunocapture with beads or posts. A magnetic field or solid supports may aid the immunocapture. Various cell surface markers may be used for immunocapture, including EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, or Leukocyte Associated Receptor (LAR).

Immunomagnetic capture, also known as immunomagnetic cell separation typically involves attaching antibodies directed to proteins found on a particular cell type to small paramagnetic beads. When the antibody-coated beads are mixed with a sample, such as blood, they attach to and surround the particular cell. The sample is then placed in a strong magnetic field, causing the beads to pellet to one side. After removing the blood, captured cells are retained with the beads. Many variations of this general method are well known in the art and suitable for use to enrich the CTCs after they have been revealed using methods of the present invention.

In another embodiment, the revealed CTCs are further processed prior to an enrichment step using filtration. The process of revealing the CTCs breaks down aggregates of cells, thereby making the filtration more efficient.

In another embodiment, the revealed CTCs are further processed via cell separation by density gradient sedimentation. Typically, the process relies on a gross physical distinction, such as cellular density for separating nucleated cells such as CTCs from erythrocytes and other non-CTC cells. Many variations of this general method are well known in the art and suitable for use to enrich the CTCs after they have been revealed using methods of the present invention.

In another embodiment, the revealed cells are enriched by a technique called "panning". Typically, such processes utilize an antibody specific to the cell type in question in which the antibody is adhered to a solid surface. The cell mixture is layered on top of the antibody-coated surface, the targeted cells tightly adhere to the solid surface due to the immunospecific interaction involving antibody-antigen binding. Nonadherent cells are rinsed off the surface, thereby effecting a cell separation and enrichment. Cells that express a cell surface protein recognized by the antibody are retained on the solid surface whereas other cell types are not.

While the methods described in this invention are useful in revealing more CTCs, the invention also is useful in detection and characterization of CTCs. In particular, the same mechanisms that mask a CTC, including the adherence of fibrin, platelets and other cells, also make cell-surface markers less available for detection. Thus the methods for revealing more CTCs also make the cell-surface markers available for detection and characterization. The types of cell surface markers include EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, or Leukocyte Associated Receptor (LAR). In one embodiment, the methods of the invention allow better detection of these markers: In another embodiment, the methods of the invention make the characterization of cell specific markers, such as EGFR, HER2, ERCC1, CXCR4, EpCAM, E-Cadherin, Mucin-1, Cytokeratin, PSA, PSMA, RRM1. Androgen Receptor, Estrogen Receptor, Progesterone Receptor, IGF1, cMET, EML4, or Leukocyte Associated Receptor (LAR), more precise and/or accurate.

Revealing, detection, and characterization of CTCs, using the methods of the invention, is useful in assessing cancer prognosis and in monitoring therapeutic efficacy for early detection of treatment failure that may lead to disease relapse. In addition, CTC analysis according to the invention enables the detection of early relapse in presymptomatic patients who have completed a course of therapy. This is possible because the presence of CTCs has been associated and/or correlated with tumor progression and spread, poor response to therapy, relapse of disease, and/or decreased survival over a period of time. Thus, enumeration and characterization of revealed CTCs provides methods to stratify patients for baseline characteristics that predict initial risk and subsequent risk based upon response to therapy.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Accordingly, in another embodiment, the invention provides a method for diagnosing or prognosing cancer in a subject. The method includes revealing of circulating tumor cells of the subject as described herein. Revealed CTCs may then be analyzed to diagnose or prognose cancer in the subject. As such, the methods of the present invention may be used, for example, to evaluate cancer patients and those at risk for cancer. In any of the methods of diagnosis or prognosis described herein, either the presence or the absence of one or more indicators of cancer, such as, a cancer cell, or of any other disorder, may be used to generate a diagnosis or prognosis.

In one aspect, a blood sample is drawn from the patient and revealed for CTCs as described herein. Using the method of the invention, the number of CTCs in the blood sample is determined and the CTCs may be subsequently analyzed. For example, the cells may be labeled with one or more antibodies that bind to a cell adhesion molecule or cytokeratin, such as EpCAM, pan-keratin or anti-cytokeratin, and the antibodies may have a covalently bound fluorescent label. Analysis may then be performed to determine the number and characterization of CTCs in the modified sample, and from this measurement, the number of CTCs present in the initial blood sample may be determined. The number of CTCs may be determined by cytometric or microscopic techniques to visually quantify and characterize the CTCs.

In various aspects, analysis of a subject's CTC number and characterization may be made over a particular time course in various intervals to assess a subject's progression and pathology. For example, analysis may be performed at regular intervals such as one day, two days, three days, one week, two weeks, one month, two months, three months, six months, or one year, in order to track level and characterization of circulating epithelial cells as a function of time. In the case of existing cancer patients, this provides a useful indication of the progression of the disease and assists medical practitioners in making appropriate therapeutic choices based on the increase, decrease, or lack of change in circulating epithelial cells, such as the presence of CTCs in the patient's bloodstream. Any increase, be it 2-fold, 5-fold, 10-fold or higher, in the revealed CTCs over time decreases the patient's prognosis and is an early indicator that the patient should change therapy. Similarly, any increase, be it 2-fold, 5-fold, 10-fold or higher, indicates that a patient should undergo further testing such as imaging to further assess prognosis and response to therapy. Any decrease, be it 2-fold, 5-fold, 10-fold or higher, in the revealed CTCs over time shows disease stabilization and a patient's response to therapy, and is an indicator to not change therapy. For those at risk of cancer, a sudden increase in the number of circulating epithelial cells detected may provide an early warning that the patient has developed a tumor thus providing an early diagnosis. In one embodiment, the detection of revealed CTCs increases the staging of the cancer.

In any of the methods provided herein, additional analysis may also be performed to characterize circulating epithelial cells, such as CTCs, to provide additional clinical assessment. For example, in addition to image analysis and bulk number measurements, PCR techniques may be employed, such as multiplexing with primers specific for particular cancer markers to obtain information such as the type of tumor, from which the CTCs originated, metastatic state, and degree of malignancy. Additionally, cell size, DNA or RNA analysis, proteome analysis, or metabolome analysis may be performed as a means of assessing additional information regarding characterization of the patient's cancer. In various aspects, analysis includes antibodies directed to or PCR multiplexing using primers specific for one or more of the following markers: EGFR, 1-IER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, or Leukocyte Associated Receptor (LAR).

For example, the additional analysis may provide data sufficient to make determinations of responsiveness of a subject to a particular therapeutic regime, or for determining the effectiveness of a candidate agent in the treatment of cancer. Accordingly, the present invention provides a method of determining responsiveness of a subject to a particular therapeutic regime or determining the effectiveness of a candidate agent in the treatment of cancer by revealing of CTCs of the subject as described herein and analyzing the revealed CTCs. For example, once a drug treatment is administered to a patient, it is possible to determine the efficacy of the drug treatment using the methods of the invention. For example, a sample taken from the patient before the drug treatment, as well as one or more cellular samples taken from the patient concurrently with or subsequent to the drug treatment, may be processed using the methods of the invention. By comparing the results of the analysis of each processed sample, one may determine the efficacy of the drug treatment or the responsiveness of the patient to the agent. In this manner, early identification may be made of failed compounds or early validation may be made of promising compounds.

Four important indicators that provide insight to the clinical activity of candidate compounds include HER2, EGFR, CXCR4, and EphB4 RTK. HER2 provides an indicator of malignancy of a cell by determining mRNA stability and subcellular localization of HER2 transcripts. The resistance of EGFR to acquire mutations, and/or the mutations acquired provides important indicators of the activity of a candidate compound in addition to possible alternative compounds that may be used in combination with the candidate compound. An assessment of the level of DNA repair interference induced with platinum provides insight as to the status of the CXCR4 marker and metastatic condition. Additionally, assessment of the status of Ephβ4 receptor tyrosine kinase provides insight as to the metastatic potential of the cell. Accordingly, using the methods of the present invention, patients taking such candidate drugs may be monitored by taking frequent samples of blood and determining the number of circulating epithelial cells, for example CTCs, in each sample as a function of time. A further analysis of the Her2, EGFR, CXCR4, and Ephβ34 RTK indicators provides information as to pathology of the cancer and efficacy of the candidate drug. Similarly, ERRC1, Cytokeratin, PSA, PSMA, RRM1, Androgen Receptor, Estrogen Receptor, Progesterone Receptor, IGF1, cMET, EML4 and others provide insight into the clinical activity of candidate compounds. The analysis of these indicators of clinical activity may be through immunohistochemistry, fluorescent in situ hybridization (FISH), sequencing, genotyping, gene expression or other molecular analytical technique.

Analysis of revealed CTCs provide a method of determining candidate subjects for a particular clinical trial. For example, the revealed CTCs of a candidate may be analyzed to determine whether specific markers exist in order to determine whether the particular therapeutic regime of the clinical trail may be potentially successful. Accordingly in another embodiment, the invention provides a method for determining a candidate subject for a clinical trial. The method includes revealing of circulating tumor cells of the subject as described herein. The revealed cells may then be analyzed to determine whether the candidate subject is suitable for the particular clinical trial.

Analysis of revealed CTCs during a clinical trial will provide information on whether the patient is responding or not responding to the experimental drug, where no substantial change or a decrease in revealed CTCs indicates response and an increase in revealed CTCs indicates poor response. The increase or decrease may be 2-fold, 10-fold or higher. This information is an early indicator of the drug's effectiveness and may be used by the investigators as a secondary endpoint in the clinical trial.

Additionally, it is believed that because platelets, fibrin, and other clotting proteins act as a "cloak device" to protect circulating tumor cells (CTCs) in the blood from destruction, these coagulants likely promote CTCs from NK cell-mediated tumor cell death and protect them from the shear stress of blood flow while allowing CTC extravasation and growth at the secondary site. As such, it is expected that unmasking CTCs may provide an effective adjuvant to current cancer therapies by unmasking important surface recognition markers and/or antigens allowing target driven therapeutics to effectively bind and interact with the unmasked CTCs. Further, it is believed that unmasked CTCs may provide a source for therapeutic and/or prophylactic cancer vaccines. Accordingly, the present invention provides a method for treating cancer. The method includes revealing of circulating tumor cells in a subject as described herein to provide revealed (e.g., unmasked) circulating tumor cells in the subject.

In one aspect, a revealed CTC population is administered to a subject alone to provide a therapeutic and/or prophylactic cancer vaccine. The revealed CTCs may be derived from the same patient they are isolated from or from a different patient. In another aspect, the revealed CTC population may be coadministered with a therapeutic agent, such as a targeted drug or chemotherapeutic drug. Virtually any known therapeutic drug or chemotherapeutic agent may be coadministered with the revealed CTCs.

The terms "administration" or "administering" are defined to include an act of providing a compound and/or therapeutic agent, or composition of the invention to a subject in need of treatment. Administration may be via any appropriate route, depending on the type of therapeutic.

In one aspect, revealed CTCs may be coadministered with known chemotherapeutic agents, including but not limited to, Aclacinomycins, Actinomycins, Adriamycins, Ancitabines, Anthramycins, Azacitidines, Azaserines, 6-Azauridines, Bisantrenes, Bleomycins, Cactinomycins, Carmofurs, Carmustines, Carubicins, Carzinophilins, Chromomycins, Cisplatins, Cladribines, Cytarabines, Dactinomycins, Daunorubicins, Denopterins, 6-Diazo-5-Oxo-L-Norleucines, Doxifluridines, Doxorubicins, Edatrexates, Emitefurs, Enocitabines, Fepirubicins, Fludarabines, Fluorouracils, Gemcitabines, Idarubicins, Loxuridines, Menogarils, 6-Mercaptopurines, Methotrexates, Mithramycins, Mitomycins, Mycophenolic Acids, Nogalamycins, Olivomycins, Peplomycins, Pirarubicins, Piritrexims, Plicamycins, Porfiromycins, Pteropterins, Puromycins, Retinoic Acids, Streptonigrins, Streptozocins, Tagafurs, Tamoxifens, Thiamiprines, Thioguanines, Triamcinolones, Trimetrexates, Tubercidins, Vinblastines, Vincristines, Zinostatins, and Zorubicins.

The revealing of CTCs may be performed in vivo or ex vivo and reinfused and/or administered to the subject. In one aspect, revealing is performed in vivo by administration of an anti-clotting agent such as heparin, and a therapeutic agent is coadministered with the anti-clotting agent, such as a chemotherapeutic or targeted cancer drug.

In another embodiment of the invention, rather than revealing the CTCs, one may use the mask, which includes proteins, sugars, and other cells, including platelets, to find and enrich for CTCs. In this aspect, one specifically targets the mask to separate the CTCs from other components of the sample. In one example, magnetic particles with antibodies targeting fibrin bound to the particle are used to bind to the fibrin surrounding the CTCs. A magnetic field then attracts the particles with the attached CTCs, and after washing separates the CTCs from the other components of the sample. In another example, the sample flows past solid supports to which fibrin targeting antibodies are attached. These antibodies bind to the fibrin-coated CTCs separating them from the other sample components. In another example the magnetic particles or solid supports have antibodies attached that target platelet-specific cell surface proteins. These antibodies bind to platelet-coated CTCs allowing those CTCs to be separated as described above.

In another embodiment of the invention, revealed CTCs may be utilized in drug discovery or drug validation platforms. Revealed CTCs provide a useful tool to such platforms by allowing analysis of the cell surface and intracellular regions of CTCs as well as facilitating entry of drugs or down-stream effector molecules of the drug into the cell. As such, revealed CTCs may be advantageously used to screen cancer drugs or validate candidate drugs by analyzing the direct intracellular or cell surface binding of the drug. Likewise revealed CTCs may advantageously provide the ability to analyze the effects of drugs, for example, by analysis of nuclear exclusion events, such as nuclear exclusion of Androgen Receptor using receptor antagonists.

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

Protocols for Enzymatic Revealing and Imaging of CTCs

The following example illustrates specific materials and protocols to be used to provide for enriching CTCs by enzymatic treatment with plasmin and subsequent image analysis using microscopic detection.

The following materials are utilized in the protocols described in the examples as shown in Table 4 below.

TABLE 4

| Materials Used in Enzymatic Revealing and Visual Analysis Materials | |
|---|---|
| Reagents | Red blood cell lysis buffer |
| | 5% BSA in PBS |
| | 1% Paraformaldehyde |
| | 0.5% Triton-X ™ 100 |
| | Slowfade Gold ™ with DAPI ™ (Invitrogen; cat#S36938) |
| Enzymes | Plasmin (Haematologic Technologies, Inc; cat# HCPM-0140) 10 uL of plasmin (from HTI) = 75 ug/mL |
| Antibodies | EpCam-FITC ™ Human (Miltenyi Biotec; cat# 130-080-301) |
| | Biotinylated hEpCam Affinity Purified Goat igG (R&D Systems; cat# BAF960) |
| | Streptavidin Alexa Fluor 555 ™ conjugate (Invitrogen; cat# S32355) |
| - | Anti-Cytokeratin PE ™ (BD; cat# 347204) |
| | Pan-keratin (C11) Mouse mAB Alexa Fluor 488 ™ (Cell Signaling Technologies) |
| Consumables | Poly-L-Lysine slides |
| | Cell attachment slides |
| | Coverslips |

The following protocols may be used to enzymatically enrich and visually analyze CTCs in a blood sample. Specific concentrations of proteins in the fibrinolytic pathway present in whole blood that may be unmasked in the revealing process are show in Table 5 below.

TABLE 5

| Important Protein Concentrations in the Fibrinolytic Pathway (approximately 55% of whole blood is plasma) | | | |
|---|---|---|---|
| Component | Molecular Weight | Plasma Concentration (ug/mL) | Plasma Concentration (uM) |
| Fibrinogen (I) | 330,000 | 3000 | 9.09 |
| Prothrombin (II) | 72,000 | 90 | 1.388 |
| Plasminogen | 90,000 | 216 | 2.4 |
| Antiplasmin | 63,000 | 60 | 0.9524 |

Protocol 1 utilizes EpCam-FITC Human (Miltenyi Biotec; cat#130-080-301) antibodies. First, lyse 1 mL whole blood for each condition and remove lysed RBCs. Then resuspend the pellet in 5% BSA/PBS (1000 uL). Split the resuspended pellet into 2 different eppendorf tubes, 1000 uL each. Add 10 uL of plasmin to one tube and no plasmin to the other. Incubate the tubes at 37 C for 45 m. Spin down the tubes at 1000 rpm for 10 m and re-suspend in 100 uL 5% BSA/PBS.

For in solution staining, add 10 uL of the EpCam-FITC antibody and incubate in the fridge for 10 m. Bring the volume to 900 uL using BSA/PBS solution, spin 10 m, and resuspend in 400 uL PBS/BSA. Place the full volume onto one large slide (use PLL slides with hydrophobic pen to hold equivalent of 1 mL whole blood). Next, let sit for 20 m at room temperature. Decant and fix with 1% PFA for 20 m and wash with PBS. Finally, decant the liquid and mount with Slow-Fade/DAPI and coverslip before imaging.

Protocol 2 utilizes cytokeratin (BD or CST) antibodies. First lyse 1 mL whole blood for each condition and remove lysed RBCs. Resuspend the pellet in 5% BSA/PBS (1000 uL). Split the resuspended pellet into different eppendorf tubes 1000 uL each. Add 10 uL of plasmin to one tube and no plasmin to the other. Incubate the tubes at 37 C for 45 m. Next spin down at 1000 rpm for 10 m and re-suspend in 100 uL 5% BSA/PBS.

For on slide staining, bring volume to 400 uL BSA/PBS and place full volume on one large slide. Let the slide sit for 20 m at room temperature. Decant and fix with 1% PFA for 20 m then wash with PBS. Decant and permeabilize with 0.2% Triton-X 100™ for 10 m then wash with PBS. Decant and add 1:4 (BSA/PBS) of CK for 30 m then wash with PBS. Next DAPI mount on the slide.

Protocol 3 utilizes biotinylated EpCam antibody and Steptavidin Alexa. First lyse 1 mL whole blood for each condition and remove lysed RBCs. Resuspend the pellet in 5% BSA/PBS (1000 uL). Split the resuspended pellet into different eppendorf tubes 1000 uL each. Add 10 uL of plasmin to one tube and no plasmin to the other. Incubate the tubes at 37 C for 45 m. Next spin down at 1000 rpm for 10 m and re-suspend in 100 uL 5% BSA/PBS.

For in solution staining, add 10 uL of the EpCam-Biotin antibody and incubate in the fridge for 10 m. Bring the volume to 1000 uL BSA/PBS solution, spin 5 m and resuspend in 1000 uL PBS/BSA. Add 0.5 uL of Streptavidin-Alexa and incubate in the fridge for 20 m. Then bring the volume to 1000 uL BSA/PBS solution, spin 5 m and resuspend in 1000 uL PBS/BSA. Place the full volume onto one large slide (use PLL slides with hydrophobic pen to hold equivalent of 1 mL whole blood) and let sit for 20 m at room temperature. Decant and fix with 1% PFA for 20 m and then wash with PBS. Next decant the liquid and mount with SlowFade/DAPI, coverslip before imaging and image analysis using a fluorescent microscope, computers and computer algorithms.

Example 2

Enzymatic Revealing and Imaging of Unmasked CTCs

The following experiment was performed using the materials presented in Example 1. The following example describes generation of a revealed population of unmasked CTCs produced from blood samples taken from a patient with breast cancer. The revealed samples were subsequently imaged using microscopic detection.

Three samples were prepare as follows: 1) HD drawn the day of (negative control); 2) cancer patient drawn the day of (B8 progressive); and 3) HD with HT29 cells (positive control). For each sample, 3 mL of whole blood was lysed for each condition and lysed RBCs were removed. Next the pellet was resuspeded in 5% BSA/PBS (3000 uL) and each sample was split into 3 eppendorf tubes at 1000 uL each. For each sample split, 1 uL of plasmin (HTI) was added to one tube and incubated for 45 m at room temperature, 10 uL of plasmin was added to a second tube and incubated for 45 m at room temperature, and no plasmin was added to a third tube. After incubation the tubes were spun down at 1000 rpm for 10 m and resuspended in 100 uL 5% BSA/PBS.

In solution staining was performed by addition of 10 uL to each tube of the HEA-FITC antibody and incubation in the fridge for 10 m. The volumes were then brought to 900 uL with BSA/PBS solution, spun for 10 m and then resuspended in 400 uL PBS/BSA. The full volumes of each tube were each placed on one large slide for each (PLL slides with hydrophobic pen to hold equivalent of 1 mL whole blood) and let to sit for 10 m in 4 C. The slides were decanted and fixed with 2% PFA for 20 m. Finally, the liquid was decanted and the slides mounted with SlowFade/DAPI, and coversliped before imaging.

To image the slides, first, 60× objective was used to pan around the slide, looking for cells in the cancer patient that were brighter than background. Once this first cell was located, the same cell was viewed using the 10× objective. This was repeated until eyes were trained to pick out such cells at 10×. Then 10× was used to pan across the slide, changing to 60× when a potential EpCam+ cell was identified.

Figure 7:
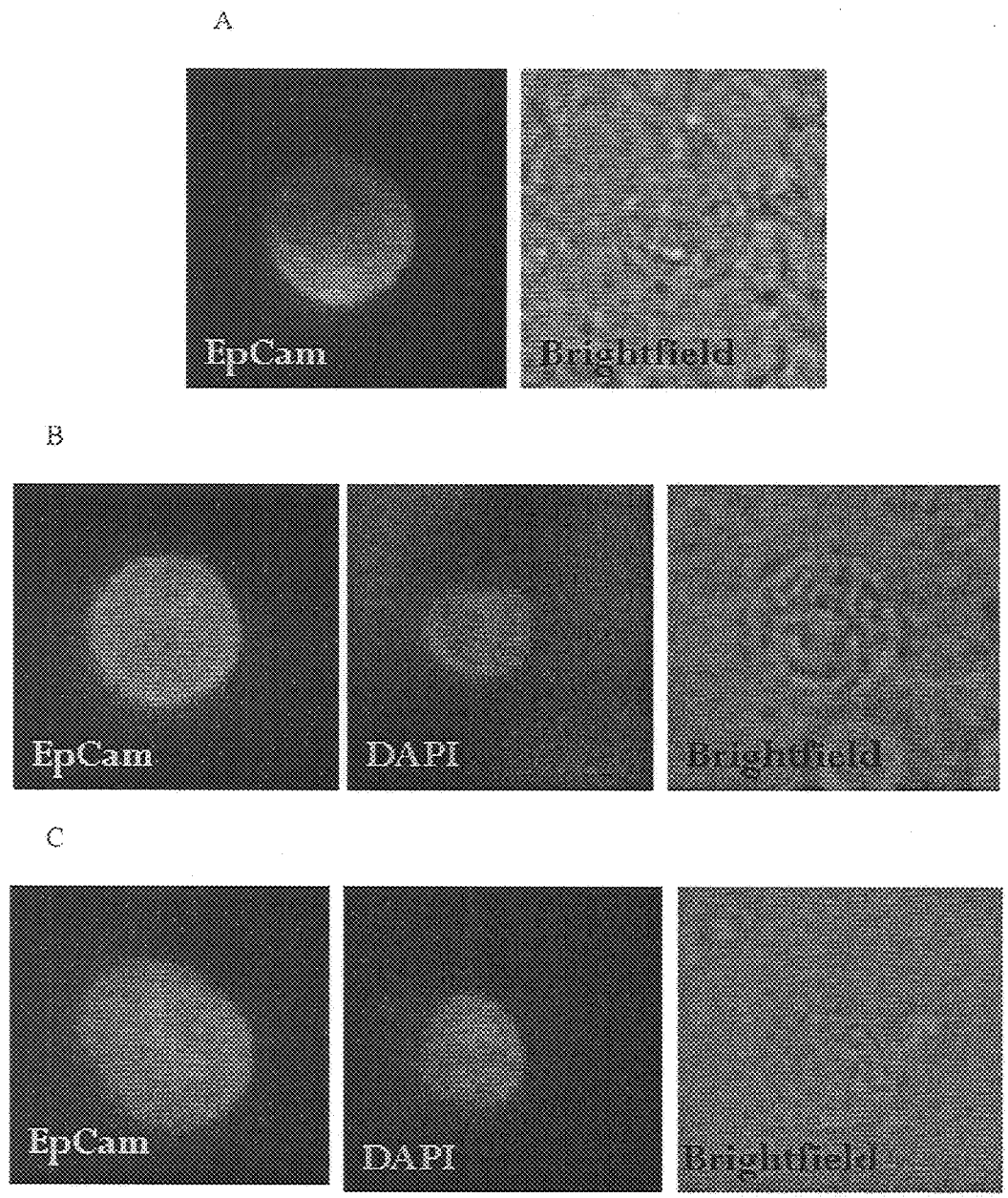
FIGS. 7A-C are pictorial representations showing slide images of revealed CTCs from blood of a breast cancer patient.
Figure 8:
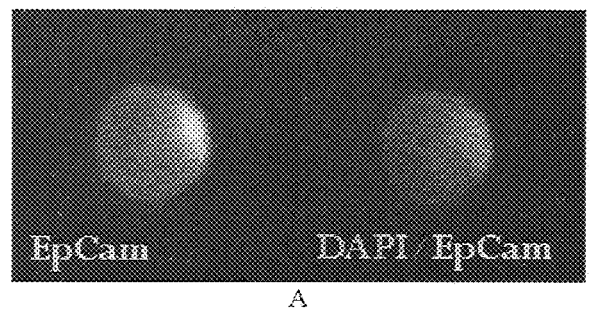
FIGS. 8A-C are pictorial representations showing slide images of revealed CTCs from blood of a breast cancer patient.
Figure 8:
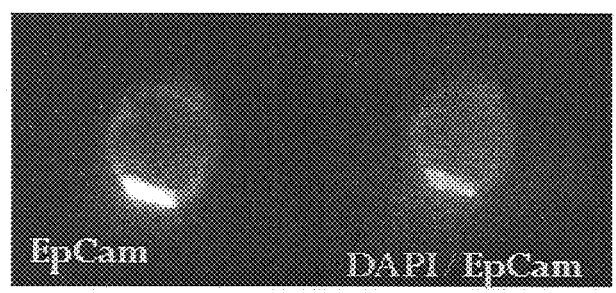
Figure 8:
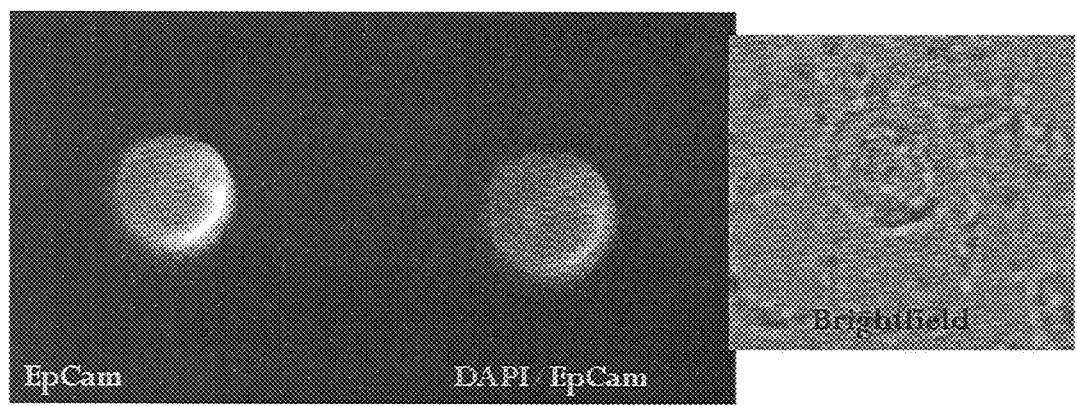
Figure 9:
FIGS. 9A-C are pictorial representations showing slide images of CTCs from blood of a breast cancer patient.
Figure 9:
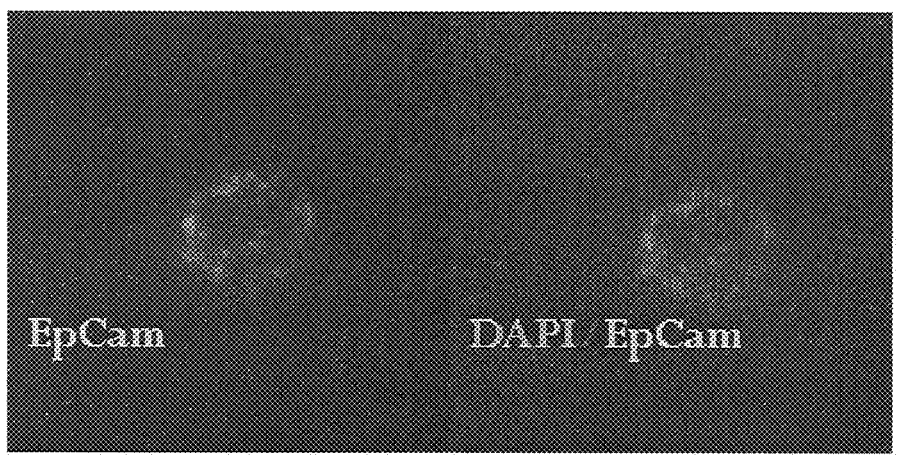
Figure 9:
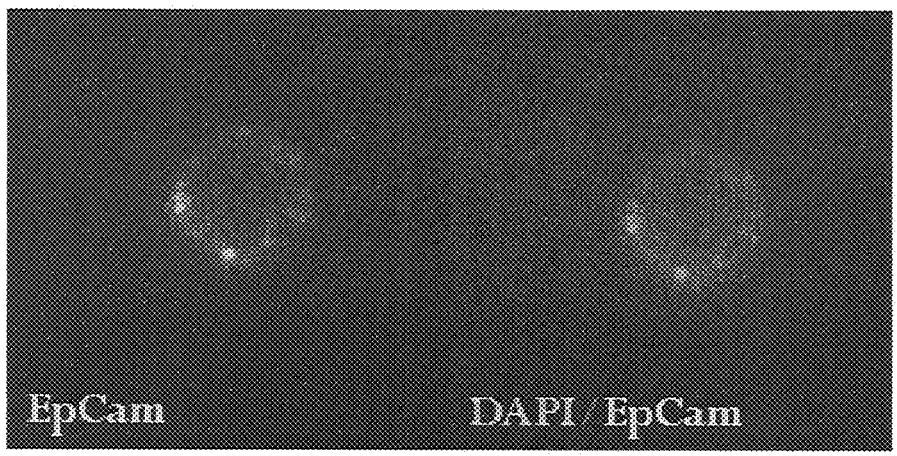

Results are shown in FIGS. 7-9. FIGS. 7A-C show slide images of sample 2 (breast cancer patient) using 1× plasmin concentration. An estimation of 1 CTC per mL was observed. An average of 3 cells per horizontal scan across the slide at 10× was performed. The results are as follows for slides A to E: A) 1; B) 5-8; C) 4; D) 5; and E) 1. These were all verified at 60×. Using these observation it is estimated that approximately 75 revealed CTCs were present per mL which is equivalent to 750 CTCs per 10 ml of blood.

Figure 10:
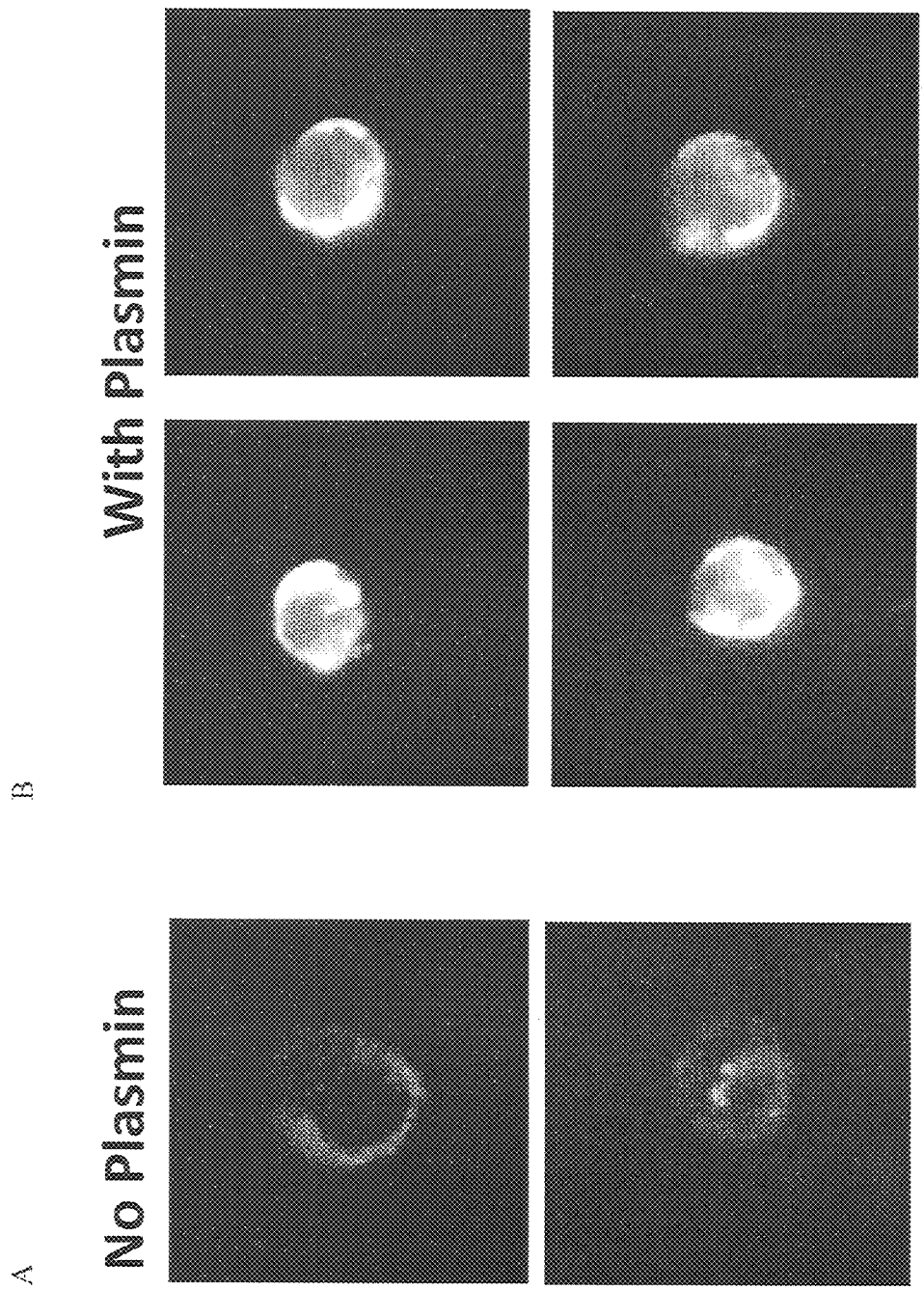
FIGS. 10A-B are pictorial representations showing slide images of CTCs from blood of a breast cancer patient.

FIGS. 8A-C show slide images of sample 2 (breast cancer patient) using 10× plasmin concentration. FIGS. 9A-C show slide images of sample 2 (breast cancer patient) using no plasmin. Note that blotchy, granular type EpCam staining with reduced clarity is observed in images of samples without treatment using plasmin as compared to slides of the plasmin treated samples. FIGS. 10A-B show slide images of sample 2 (breast cancer patient) using plasmin (FIG. 10A) versus no plasmin (FIG. 10B). It was observed that plasmin treatment enhanced signal to noise and resolved bleaching complications.

Results of using plasmin treatment and t-PA treatment are shown in Tables 6 and 7 below.

TABLE 6

Results Using Plasmin

| Trial | Enzyme | # cells/ml | Comments |
|---|---|---|---|
| I | 7.5 µg plasmin-CP | Yes (75/ml) | Plasmin treatment works |
| I | 7.5 µg plasmin-HD | Yes | Plasmin treatment works |
| I | 7.5 µg plasmin-HD | No | Plasmin treatment works |
| I | 7.5 µg plasmin-CP | No | Plasmin treatment works |

TABLE 7

Results Using t-PA

| Trial | Enzyme | # cells/mL | Comments |
|---|---|---|---|
| I | 1 uL tPA | n/a | EpCam+ cells found in decant |
| II | 0 uL tPA | 8 | EpCam+ cells found in decant |
| II | 1 uL tPA | 80 | EpCam+ cells found in decant |
| III | 0 uL tPA | 32 | |
| III | 1 uL tPA | 28 | |

Although the invention has been described with reference to the above example, it will be understood that modifications and variations are encompassed within the spirit and scope of the invention. Accordingly, the invention is limited only by the following claims.

What is claimed is:

1. A method for revealing circulating tumor cells in a sample obtained from a subject comprising:
   a) obtaining a sample from the subject;
   b) removing or degrading a protein, carbohydrate, cell, or a combination thereof, in physical association with the surface of the circulating tumor cells present in the sample, wherein the circulating tumor cells remain intact, thereby unmasking and revealing the circulating tumor cells in the sample; and c) analyzing one or more circulating tumor cells of (b), the analysis comprising characterizing morphology of the one or more circulating tumor cells via image analysis.

2. The method of claim 1, wherein revealing the cells comprises removing all or portions of blood plasma proteins, platelets, or a combination thereof.

3. The method of claim 2, wherein the blood plasma protein is a clotting factor.

4. The method of claim 3, wherein the clotting factor is fibrin.

5. The method of claim 1, wherein the cells are treated enzymatically, mechanically, electrically, electromagnetically, chemically, or any combination thereof.

6. The method of claim 5, wherein the cells are treated enzymatically.

7. The method of claim 6, wherein the enzymatic treatment is by fibrinolysis.

8. The method of claim 7, wherein fibrinolysis is with plasmin.

9. The method of claim 7, wherein enzymatic treatment is by incubation with an animal venom or a toxin.

10. The method of claim 9, wherein the animal venom or toxin is naturally occurring or synthetically derived from a snake or a bat.

11. The method of claim 5, wherein enzymatic treatment is by activation of plasminogen.

12. The method of claim 1, wherein treatment of the cells is performed using an anti-coagulant or a blood thinner.

13. The method of claim 1, wherein the number of revealed circulating tumor cells is increased by a factor of at least 2, 5, 10, 20, 30, 40, 50, 60, 70, 80, 90, 100, or 200.

14. The method of claim 1, wherein the sample is about 200 microliters.

15. The method of claim 1, wherein the revealed cells comprise greater than about 7.5 circulating tumor cells per 100 microliters.

16. The method of claim 1, further comprising enriching the sample.

17. The method of claim 16, wherein the sample is enriched immunomagnetically or by filtration.

18. The method of claim 1, further comprising cell number analysis, polymerase chain reaction (PCR) analysis, sequence analysis, DNA analysis, RNA analysis, gene expression profiling, proteome analysis, metabolome analysis, immuno assays, nuclear exclusion analysis.

19. The method of claim 1, wherein the image analysis comprises detection of a cell surface marker.

20. The method of claim 19, wherein the cell surface marker is selected from the group consisting: EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, or Leukocyte Associated Receptor (LAR).

21. The method of claim 19, wherein antibodies are used to detect the cell surface markers.

22. The method of claim 21, wherein the antibodies are fluorescently labeled.

23. The method of claim 22, wherein the antibodies are directed to EpCAM, Cytokeratin, or a combination thereof.

24. The method of claim 1, wherein the image analysis is performed by microscopy or flow cytometry.

25. The method of claim 18, wherein the PCR analysis comprises multiplexing using primers specific for genes selected from the group consisting of EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, or Leukocyte Associated Receptor (LAR).

26. The method of claim 18, wherein the nuclear exclusion analysis comprises nuclear exclusion of the Androgen Receptor.

27. The method of claim 1, further comprising providing a diagnosis and prognosis to a subject from which the sample was taken.

28. The method of claim 1, wherein the subject is known to have cancer and is undergoing cancer therapy.

29. The method of claim 28, wherein the therapy is chemotherapy.

30. The method of claim 28, wherein the subject is being administered a candidate agent.

31. The method of claim 28, further comprising determining the responsiveness of the subject to the cancer therapy.

32. A method of detecting tumor cell type of a circulating tumor cell in a sample from a subject comprising:

a) removing or degrading a protein, carbohydrate, cell, or a combination thereof, in physical association with the surface of the circulating tumor cell present in the sample, wherein the circulating tumor cell remains intact, thereby unmasking and revealing the circulating tumor cell in the sample; and b) analyzing the circulating tumor cell of (a) to determine cell type of the circulating tumor cell.

33. The method of claim 32, wherein analyzing comprises image analysis, cell number analysis, cell morphology analysis, polymerase chain reaction (PCR) analysis, sequence analysis, DNA analysis, RNA analysis, gene expression profiling, proteome analysis, metabolome analysis, immuno assays, nuclear exclusion analysis.

* * * * *